(12) United States Patent
Hansen et al.

(10) Patent No.: US 11,021,820 B2
(45) Date of Patent: Jun. 1, 2021

(54) NONWOVEN FABRIC COMPRISING A HIGH LOFT SPUNBOND LAYER

(71) Applicants: Fibertex Personal Care A/S, Aalborg (DK); Reifenhauser GmbH & Co. KG Maschinenfabrik, Troisdorf (DE)

(72) Inventors: Morten Rise Hansen, Aalborg (DK); Thomas Broch, Gistrup (DK); Sebastian Sommer, Troisdorf (DE)

(73) Assignees: FIBERTEX PERSONAL CARE A/S, Aalborg (DK); REIFENHAUSER GMBH & CO. KG MASCHINENFABRIK, Troisdorf (DE)

(*) Notice: Subject to any disclaimer, the term of this patent is extended or adjusted under 35 U.S.C. 154(b) by 97 days.

(21) Appl. No.: 15/597,174

(22) Filed: May 17, 2017

(65) Prior Publication Data
US 2017/0335498 A1  Nov. 23, 2017

(30) Foreign Application Priority Data
May 18, 2016 (EP) .................................. 16170156

(51) Int. Cl.
*D04H 1/74* (2006.01)
*D04H 3/007* (2012.01)
(Continued)

(52) U.S. Cl.
CPC .......... *D04H 1/74* (2013.01); *A61F 13/5148* (2013.01); *A61F 13/51478* (2013.01);
(Continued)

(58) Field of Classification Search
CPC . A61F 13/51478; A61F 13/5148; D02G 3/04; D04H 1/50; D04H 1/56; D04H 1/74; D04H 3/007; D04H 3/147; D04H 3/16
See application file for complete search history.

(56) References Cited

U.S. PATENT DOCUMENTS

| | | | |
|---|---|---|---|
| 6,368,444 B1 | 4/2002 | Jameson et al. | |
| 6,723,669 B1 * | 4/2004 | Clark | D04H 3/16 442/329 |

(Continued)

FOREIGN PATENT DOCUMENTS

| | | |
|---|---|---|
| CN | 102197171 A | 9/2011 |
| EP | 0989222 A1 | 3/2000 |

(Continued)

OTHER PUBLICATIONS

Extended European Search Report issued in corresponding European Patent Application No. 16170156.0 dated Nov. 23, 2016 (7 pages).

(Continued)

*Primary Examiner* — Arti Singh-Pandey
(74) *Attorney, Agent, or Firm* — Kilyk & Bowersox, P.L.L.C.

(57) ABSTRACT

The invention relates to a fabric comprising at least one high loft spunbond nonwoven layer having crimped multicomponent fibers, wherein a first component of the multicomponent fibers comprises a first polymer A and a second component of the multicomponent fibers comprises a blend of the first polymer A and a second polymer B, wherein the melt flow rate of polymer A is at least 25% higher than the melt flow rate of polymer B and wherein the second component comprises at least 40 wt.-% of polymer B.

19 Claims, 7 Drawing Sheets

Figure 1:
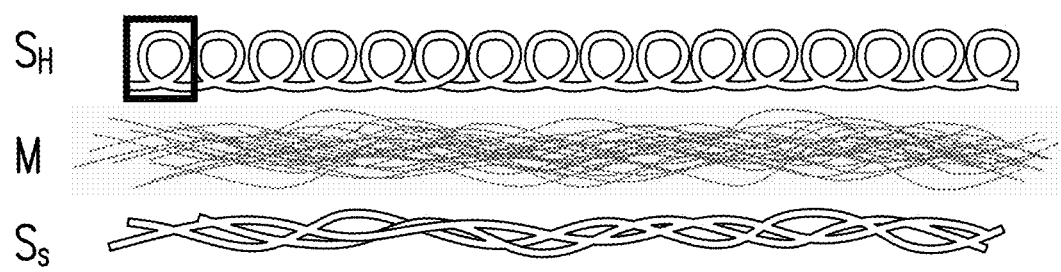

(51) Int. Cl.
  *D04H 3/147*   (2012.01)
  *D04H 1/50*    (2012.01)
  *D02G 3/04*    (2006.01)
  *D04H 1/56*    (2006.01)
  *D04H 3/16*    (2006.01)
  *A61F 13/514*  (2006.01)
(52) U.S. Cl.
  CPC ............... *D02G 3/04* (2013.01); *D04H 1/50* (2013.01); *D04H 1/56* (2013.01); *D04H 3/007* (2013.01); *D04H 3/147* (2013.01); *D04H 3/16* (2013.01)

(56)          References Cited

U.S. PATENT DOCUMENTS

2003/0136254 A1   7/2003   Hirano et al.
2004/0116027 A1   6/2004   Termonia et al.
2004/0201125 A1  10/2004   Allen et al.
2010/0228214 A1   9/2010   Bornemann et al.
2011/0189915 A1   8/2011   Morimoto et al.

FOREIGN PATENT DOCUMENTS

EP     3121314    A1   1/2017
JP     2013049943 A    3/2013
WO     9621562    A1   7/1996
WO     9916947    A1   4/1999
WO     0028123    A1   5/2000
WO     2015141750 A1   9/2015

OTHER PUBLICATIONS

Office Action issued in corresponding Chinese Patent Application No. 201710354053.7 dated Oct. 10, 2020 (13 pages).

* cited by examiner

NONWOVEN FABRIC COMPRISING A HIGH LOFT SPUNBOND LAYER

The present invention relates to a nonwoven fabric comprising at least one high loft spunbond layer having crimped multicomponent fibers. The invention further relates to a hygiene product comprising such nonwoven fabric.

High loft spunbond layers may contribute to the provision of nonwoven fabrics having a high softness as desired in hygiene products such as diapers, sanitary napkins and the like. Nonwoven fabrics comprising high loft spunbond layers on the basis of crimped fibers are known in the art.

One such fabric is described in U.S. Pat. No. 6,454,989 B1. The crimp of the fibers is thereby achieved upon using multicomponent fibers where the two components have different melt flow rates. Another such fabric is described in EP 2 343 406 B1. The crimp of the fibers is thereby achieved upon using multicomponent fibers where the two components have similar melt flow rates and melting points, but a certain difference in the ratio of Z-average to weight average molecular weight distributions.

The purpose of the invention is to provide spunbond fibers having an improved crimp and a spunbond nonwoven fabric having a higher loft as compared to these known products while maintaining other desirable properties such as stability and liquid barrier.

Against this background the invention pertains to a fabric comprising at least one high loft spunbond nonwoven layer ($S_H$) having crimped multicomponent fibers. According to the invention, a first component of the multicomponent fibers comprises a first polymer A and a second component of the multicomponent fibers comprises a blend of the first polymer A and a second polymer B. The melt flow rate of polymer A is at least 25% higher than the melt flow rate of polymer B. The second component comprises at least 40 wt.-% of polymer B.

It has surprisingly been found out that the loft of the spunbond layers can be improved if the second component does not only comprise a polymer B which has a melt flow rate different from the melt flow rate of the polymer A of the first component, such as in U.S. Pat. No. 6,454,989 B1, but comprises a blend of such polymer B with the same polymer A which is used in the first component. In terms of producing a spunbond nonwoven this means that when making a blend of the two polymers A and B of different melt flow rates in one polymer stream in, e.g., a side-by-side arrangement and maintaining polymer A in the other polymer stream, an increased crimp of the fiber is seen. This effect has been observed when the second component comprised a significant amount of polymer B, i.e., an amount of at least 40 wt.-%.

While multicomponent fibers where a first component comprises a first polymer A and a second component comprises a blend of the first polymer A and a small amount of a second polymer B have been tested in EP 2 343 406 B1, this reference aims to maintain a similar melt flow rate for both components and does not teach that using polymer A also for the second component could bring about advantages specifically when polymers of different melt flow rates are used.

The term 'high loft' spunbond layer is used herein simply to name the respective spunbond layer, which will have a certain degree of loft due to the crimped fibers. The term, however, is merely qualitative and does not imply a certain minimum degree of loft.

The high loft spunbond layer may comprise or consist of the crimped multicomponent fibers. The crimped fibers may, for example, be helically crimped.

The melt flow rate of polymer A is at least 25% higher than the melt flow rate of polymer B. The difference can also be 35% or greater for enhanced effects.

In one embodiment the melt flow rate of polymer A is smaller or equal 26 g/10 min and the melt flow rate of polymer B is 34 g/10 min or greater.

The high loft of the fabric may contribute to an improved feel, which is desirable, for example, in hygiene applications. A high loft may also contribute to avoid or minimize glue bleed through during the manufacture of articles such as hygiene products from nonwoven fabrics.

The fabric may consist of the high loft spunbond nonwoven ($S_H$) layer or alternatively be a laminate comprising more than one high loft layers and/or different nonwoven layers, polymeric films or the like.

In one embodiment the fabric further comprises at least one meltblown layer (M) and/or at least one standard loft spunbond layer ($S_S$), where these additional layers form a nonwoven laminate with the at least one high loft layer spunbond layer ($S_H$), preferably an SMS-type nonwoven laminate.

The term 'standard loft' is used herein simply to name the respective other spunbond nonwoven layer, which will have a lower degree of loft due to traditional non-crimped and usually monocomponent fibers. Also this term, however, is merely qualitative and does not imply a certain maximum degree of loft. The invention provides, however, that the density of the high loft spunbond layer is lower than the density of the high loft nonwoven layer.

In one embodiment, additional meltblown layer(s) can be formed on one or both surfaces of the $S_H$ layer. As the crimped fibers of the $S_H$ layers may entangle with a substrate, e.g. the spinbelt in fabric production, applying a meltblown cover may improve release properties.

In one embodiment, the fabric comprises at least one melt blown layer (M) sandwiched between at least one standard loft spunbond layer ($S_S$) and the at least one high loft spunbond layer ($S_H$). Possible such SMS-type laminates comprise $S_H M S_H$, $S_S M M S_H$, $S_S S_S M S_H$, $S_S M S_H S_H$, $S_S S_S M M S_H$, $S_S M M S_H S_H$, $S_S S_S M M S_H S_H$ etc. laminates.

The standard loft spunbond layers ($S_S$) may contribute to an improved mechanical stability of the laminate, e.g., to an improved stability against rupturing and puncturing. The meltblown layers (M) may contribute to an improved barrier property which is desirable, e.g., for barrier legcuffs of hygiene products.

In this embodiment, the invention envisions to combine good barrier properties with a soft and bulky textile character of the nonwovens by means of combining 'traditional' spunbond nonwovens with spunbond nonwovens comprising crimped fibers according to the invention.

Of course, in an alternative embodiment, in each of the above SMS-laminates, another $S_H$ may be used instead of the (or each) $S_S$ layer ($S_H M S_H$ and so forth). This is particularly interesting for products were a high level of masking is desired.

In one embodiment, where the method of the invention forms part of an overall process to form a layered nonwoven fabric, the layered fabric may comprise at least one standard loft spunbonded layer and at least one high loft spunbonded layer formed in agreement with the invention. Resulting fabrics may be of the general type $S_H S_S S_H$ (including variants such as $S_H S_S S_S S_H$, $S_H S_S S_H S_H$, $S_H S_S S_S S_H S_H$ and so forth). In this embodiment, a sandwich structure comprising a first high loft spunbonded layer ($S_H$) and a center layer based on standard spunbond ($S_S$) followed by another high loft spunbonded layer ($S_H$) layer is obtained. This would lead to a structure where, as compared to a spunmelt $S_H M S_H$ structure, the meltblown (M) center layer is replaced with an $S_S$ layer. Adding a layer of essentially uncrimped standard spunbond nonwoven $S_S$ sandwiched in between two or more layers of high loft spunbonded fabric ($S_H$) leads to an increase in strength and stability to the material. At the same time, both outer layers of the embodiments exhibit desirably high softness from the high loft spunbonded fabric ($S_H$).

In yet another embodiment, resulting fabrics may be of the general type $S_H S_S$ (including variants such as $S_S S_H$, $S_S S_H S_H$, $S_S S_S S_H S_H$ and so forth). In this embodiment, a layer structure comprising a first standard loft spunbonded base layer ($S_S$) and high loft spunbonded top layer ($S_H$) layer is obtained. Again, adding layer(s) of essentially uncrimped standard spunbond nonwoven $S_S$ to layer(s) of high loft spunbonded fabric ($S_H$) leads to an increase in strength and stability to the material, while the top layer exhibits desirably high softness.

In one embodiment, the multicomponent fibers are bicomponent fibers consisting of the first and second components.

In one embodiment, the first and second components are arranged in a side-by-side or eccentric sheath/core arrangement. The term "side-by-side" arrangements includes variants such as, for example, hollow side-by-side arrangements, eccentric hollow side-by-side arrangements and side-by-side multilobal arrangements. Also numerous other fiber shapes and cross-sectional configurations are suitable for use with the present invention.

In one embodiment, the first component constitutes the core component in the sheath-core arrangement. In another embodiment, the first component constitutes the sheath component in the sheath-core arrangement.

In one embodiment the first polymer A is a thermoplastic polymer.

In one embodiment the second polymer B is a thermoplastic polymer.

Suitable thermoplastic polymers comprise polyolefin polymers. Suitable polyolefin polymers for both A and B comprise polypropylene (PP) and polyethylene (PE) polymers and copolymers and blends thereof. For both A and B, PP homopolymers are particularly preferred.

In one embodiment the melt blown layer (M) is made of a thermoplastic polymer.

In one embodiment the standard loft spunbond layer ($S_S$) is made of a thermoplastic polymer.

Also in this regard, suitable thermoplastic polymers comprise polyolefin polymers and suitable polyolefin polymers comprise polypropylene (PP) and polyethylene (PE) polymers and copolymers and blends thereof. PP homopolymers are particularly preferred.

The polymers used for the $S_S$ and the M layer may be the same or may be different from one another and may be the same or different from the polymer A or the polymer B. In one embodiment, the polymer used for the standard loft spunbond layer ($S_S$) is identical to polymer A. Additionally or alternatively, the polymer used for the melt blown layer (M) may be different from the polymer A and may also be different from the polymer B. All polymers used in the fabric may be polyolefin polymers as described above, with PP homopolymers being particularly preferred in each case.

In one embodiment the second polymer B may have a molecular weight distribution different from the molecular weight distribution of the first polymer A. Such difference in molecular weight distribution may contribute to the degree of crimp in the fibers while at the same time the tensile and elongation properties remain on an equal level.

The difference in molecular weight distribution (MWD) between polymer A and polymer B may be expressed in terms of, e.g., a difference in the polydispersity indices ($M_W/M_N$) or a difference in the ratios of $M_Z/M_W$.

For example, the second polymer B may have a broader molecular weight distribution than the first polymer A. Alternatively the second polymer B may have a narrower molecular weight distribution than the first polymer A.

In one embodiment the second polymer B and the first polymer A have a different level of crystallinity. This may also contribute to a higher loft.

In one embodiment the difference in polydispersity indices between the polymers A and B is greater than 0.5. In a different embodiment, higher differences such as greater than 1.0 or greater than 1.5 are employed.

In one embodiment the polydispersity index of polymer A is between 4.0 and 6.0 and preferably between 4.3 and 5.3 and/or wherein the polydispersity index of polymer B is between 5.5 and 7.5 and preferably between 6.3 and 7.0.

In one embodiment the weight ratio of polymers A to B in the second component is 60/40 to 20/80, more preferably 60/40 to 30/70 and still more preferably 60/40 to 40/60.

The content of the first polymer A in the second component may be 40 wt.-% to 80 wt.-%, preferably 40 wt.-% to 70 wt.-% and still more preferably 40 wt.-% to 60 wt.-%. The content of the second polymer B may be 20 wt.-% to 60 wt.-%, preferably 30 wt.-% to 60 wt.-% and still more preferably 40 wt.-% to 60 wt.-%.

In one embodiment, the second component consists of polymers A and B and, optionally, the optional components described herein.

In one embodiment the weight ratio of the first to second component in the multicomponent fibers is 40/60 to 90/10, preferably 60/40 to 80/20 and more preferably 65/35 to 75/25. The content of the first component in the multicomponent fibers may be 40 wt.-% or more, preferably 50 wt.-% or more, more preferably 60 wt.-% or more and still more preferably 65 wt.-% or more. The first component may constitute the main component of the multicomponent fibers. The above values alternatively apply to vol.-%, which are sometimes easier to determine in this case. This means than, on average, the first component may in one embodiment be present over 40% etc. or more of the cross-sectional area of the multicomponent fibers.

In one embodiment, the crimped multicomponent fibers are bicomponent fibers and consist of the first and the second component.

In one embodiment the polymer of the first component and/or the polymer blend of the second component and/or the polymer of the $S_S$ layer and/or the polymer of the M layer comprise an additive which is capable of enhancing the softness of the fiber. This agent is preferably a slip agent which may be selected from the group of unsaturated fatty acids. Suitable slip agents comprise, for example, oleamide and erucamide fatty acid derivatives.

Alternatively or additionally, the respective polymers may comprise a coloring additive such as, for example, $TiO_2$ or other functional additives like wetting or antistatic agents.

In one embodiment, each additive may be present in an amount of, e.g., up to 5 wt.-%, up to 2 wt.-% or up to 1 wt.-%. The first component may consist of the first polymer and, optionally, an additive. The second component may consist of the first and second polymer and, optionally, an additive.

In one embodiment the linear mass density of the crimped multicomponent fibers is 1.4 to 2.6 and preferably 1.4 to 2.2 denier. If present, also the fibers of the standard loft spunbond layer(s) ($S_S$) may comprise a linear mass density and/or fiber diameter in that range. The fibers of the meltblown layer(s) (M), if present, may comprise a linear mass density 0.2 to 0.5 denier and/or an average fiber diameter of 3 to 5 µm. This may contribute to a good filtering effect and good barrier property towards liquid penetration but at the same time good air permeability.

In one embodiment the average crimp diameter of the crimped multicomponent fibers is 50 to 500 µm, preferably 60 to 150 µm and more preferably 80 to 125 µm.

The fiber diameter of the crimped multicomponent fibers may be 15 to 35 µm.

In one embodiment the density of the high loft spunbond layer ($S_H$) is 0.02 to 0.08 g/cm$^3$ and preferably 0.04 to 0.06 g/cm$^3$. If present, the standard loft spunbond layer(s) ($S_S$) may have a density greater than 0.08 g/cm$^3$ and preferably greater than 1.0 g/cm$^3$.

The high loft spunbond layer(s) ($S_H$) may have a basis weight from 3 to 10 g/m$^2$. If present, the standard loft spunbond layer(s) ($S_S$) may also have a basis weight from 3 to 10 g/m$^2$. The meltblown layer(s) (M), if present, may have a combined basis weight 1 to 3 g/m$^2$.

If present, the standard loft spunbond layer(s) ($S_S$) may have a caliper of smaller than 0.12 mm and preferably smaller than 0.1 mm.

Meltblown layer(s) (M) may thus be sandwiched between a standard loft spunbond layer ($S_S$) having a regular density and the high loft spunbond layer ($S_H$) having a lower than regular density.

Against the problem identified above, the present invention further pertains to a hygiene product comprising a fabric according to the invention.

Suitable hygiene products comprise adult incontinence products, baby diapers, sanitary napkins and the like.

The hygiene products may further comprise granular absorbent material. The nonwoven according to the invention may serve as a nonwoven textile backsheet of a hygiene product which lies adjacent to the water impermeable film backsheet. Suitable granular absorbent material comprises super absorbent granulate/polymers (SAP).

The core material may comprise a high degree (e.g. more than 50, 60 or 70 wt.-%) of or consist exclusively of granular absorbent material. A high degree of granular absorbent material and a lower degree of side components, e.g., pulp/cellulose fibers results in a thinner and more comfortable product which may also require less shelf space and transport cost. As, however, the granular absorbent material gets more exposed to the backsheet, this may be perceived as negative feel by the consumer. The high loft layer(s) $S_H$ of the nonwoven according to the invention when used as a backsheet may contribute to an improved touch and feel. The high concentration of granular material in the core also leads to a greater risk for the film backsheet to be punctured by the granular absorbent material. The high oft spunbond layer(s) $S_H$ may contribute to an improved ability to withstand such puncturing.

When a laminate, e.g., an SMS-type laminate is manufactured, it may be desirable that the surface on which the (typically thin) meltblown layer is deposited, typically the surface of one of the spunbond layers, is uniform and homogenous. Otherwise the laydown uniformity and quality of the meltblown layer(s) (M) may be negatively affected and the barrier performance may be compromised. The surface of the standard loft spunbond layer ($S_S$) is typically more uniform and homogenous than the surface of the high loft spunbond layer ($S_H$).

Additionally, against the problem identified above, the present invention further pertains to a method of manufacturing an SMS-type nonwoven laminate according to the invention, which comprises the steps of providing the at least one standard loft spunbond layer ($S_S$) or high loft spunbond layer ($S_H$); forming the at least one meltblown layer (M) upon depositing meltblown fibers on the surface of the standard loft spunbond layer ($S_S$) or high loft spunbond layer ($S_H$) formed in the first step; and forming the at least one high loft spunbond layer ($S_H$) or standard loft spunbond layer ($S_S$) upon depositing spunbond fibers on the surface of the meltblown layer (M) formed in the second step.

Two $S_H$ layers may be used instead of only one $S_H$ layer, for example, when a high level of masking is desired.

The present invention further pertains to a method of manufacturing an $S_H S_S S_H$-type nonwoven according to the invention, which comprises the steps of providing the at least one high loft spunbond layer ($S_H$); forming the at least one standard loft spunbond layer ($S_S$) upon depositing spunbond fibers on the surface of the high loft spunbond layer ($S_H$) formed in the first step; and forming the at least one high loft spunbond layer ($S_H$) upon depositing spunbond fibers on the surface of the standard loft spunbond layer ($S_S$) formed in the second step.

The present invention further pertains to a method of manufacturing an $S_H S_S$-type nonwoven according to the invention, which comprises the steps of providing the at least one standard loft spunbond layer ($S_S$); and forming the at least one high loft spunbond layer ($S_H$) upon depositing spunbond fibers on the surface of the standard loft spunbond layer ($S_S$) formed in the first step.

The present invention also pertains to a method for manufacturing a hygiene product comprising manufacturing an SMS-type, $S_H S_S S_H$-type or $S_S S_H$-type nonwoven laminate in agreement with the method of the invention. The hygiene product may be characterized as above.

Figure 2:
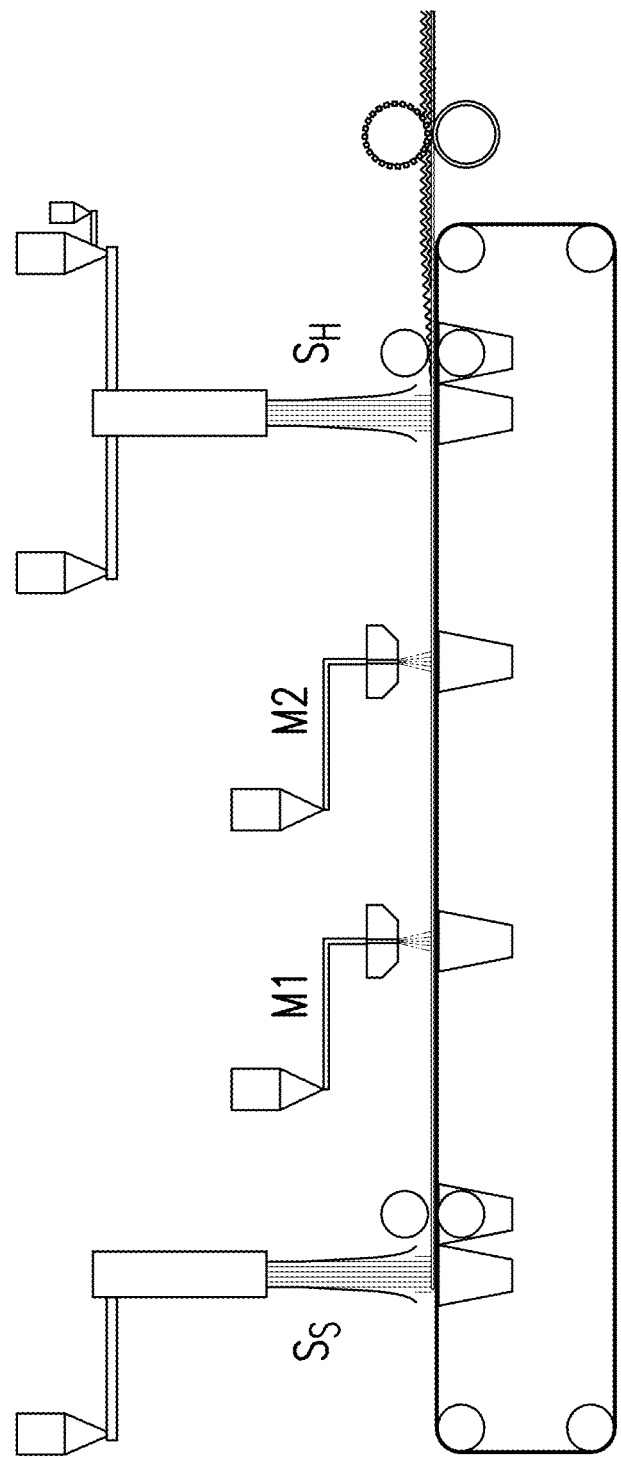
Figure 3:
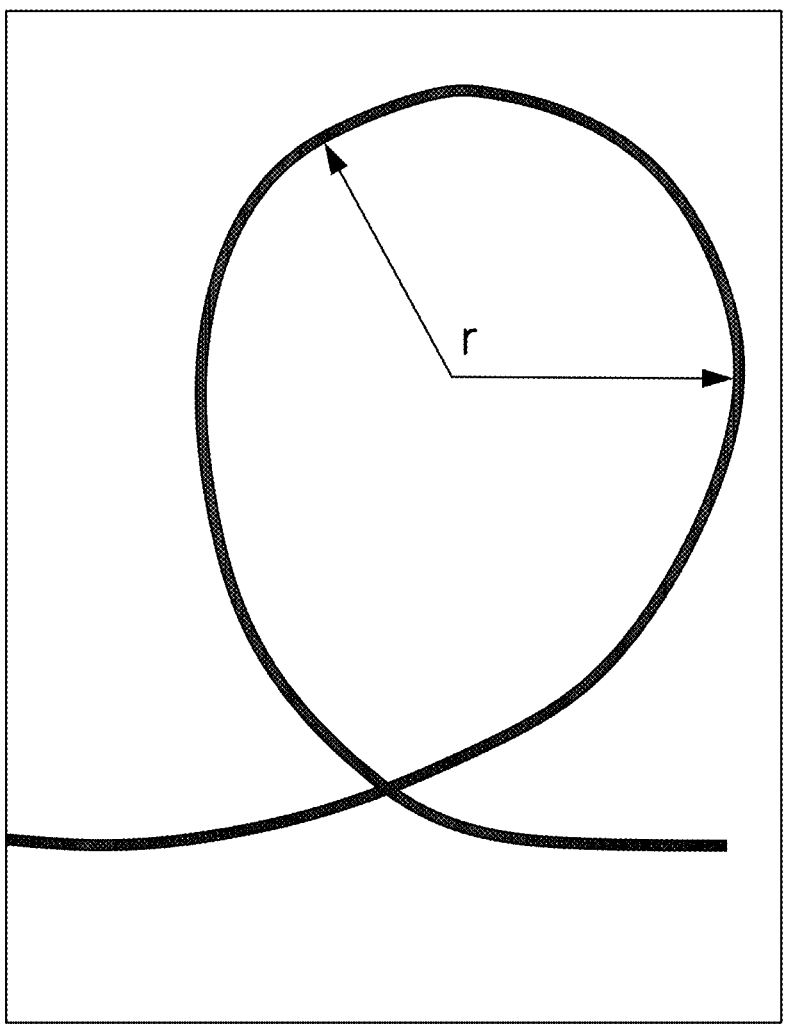
Figure 4:
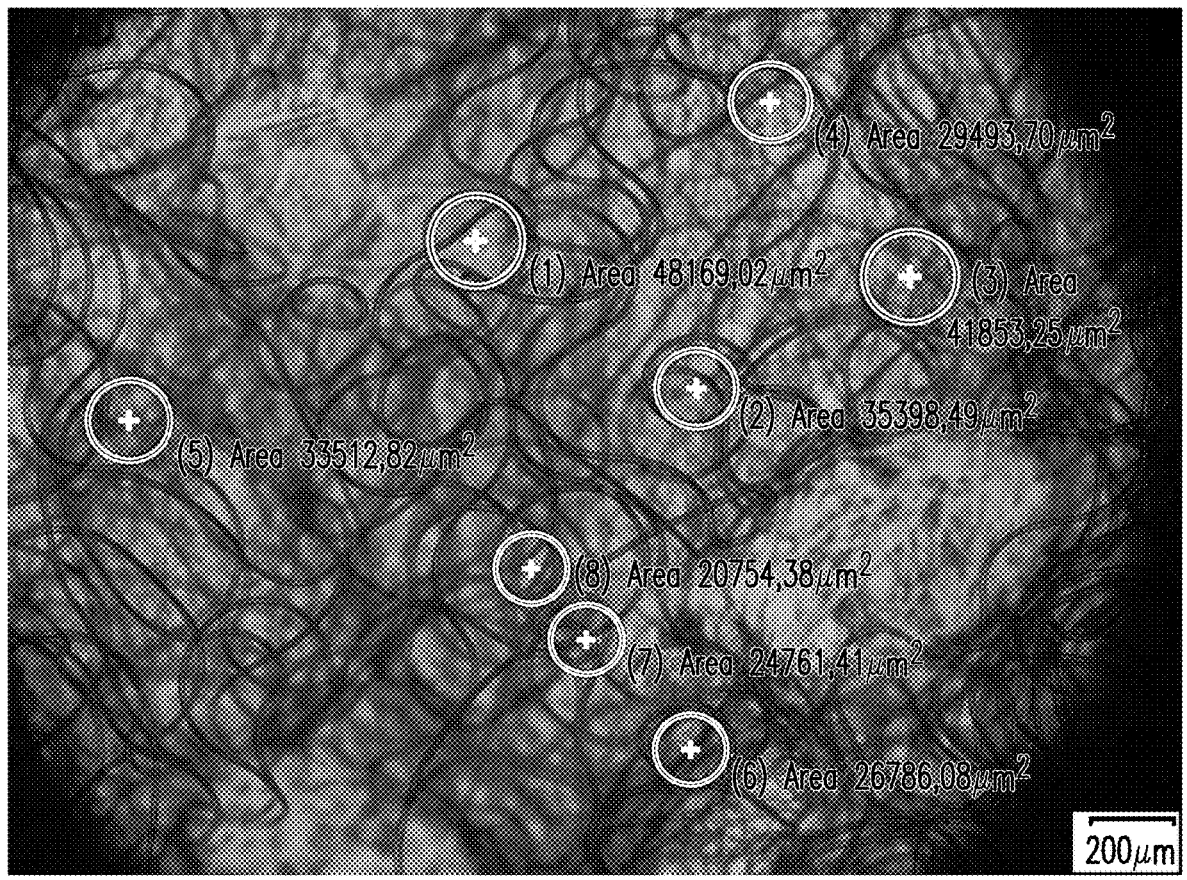
Figure 5:
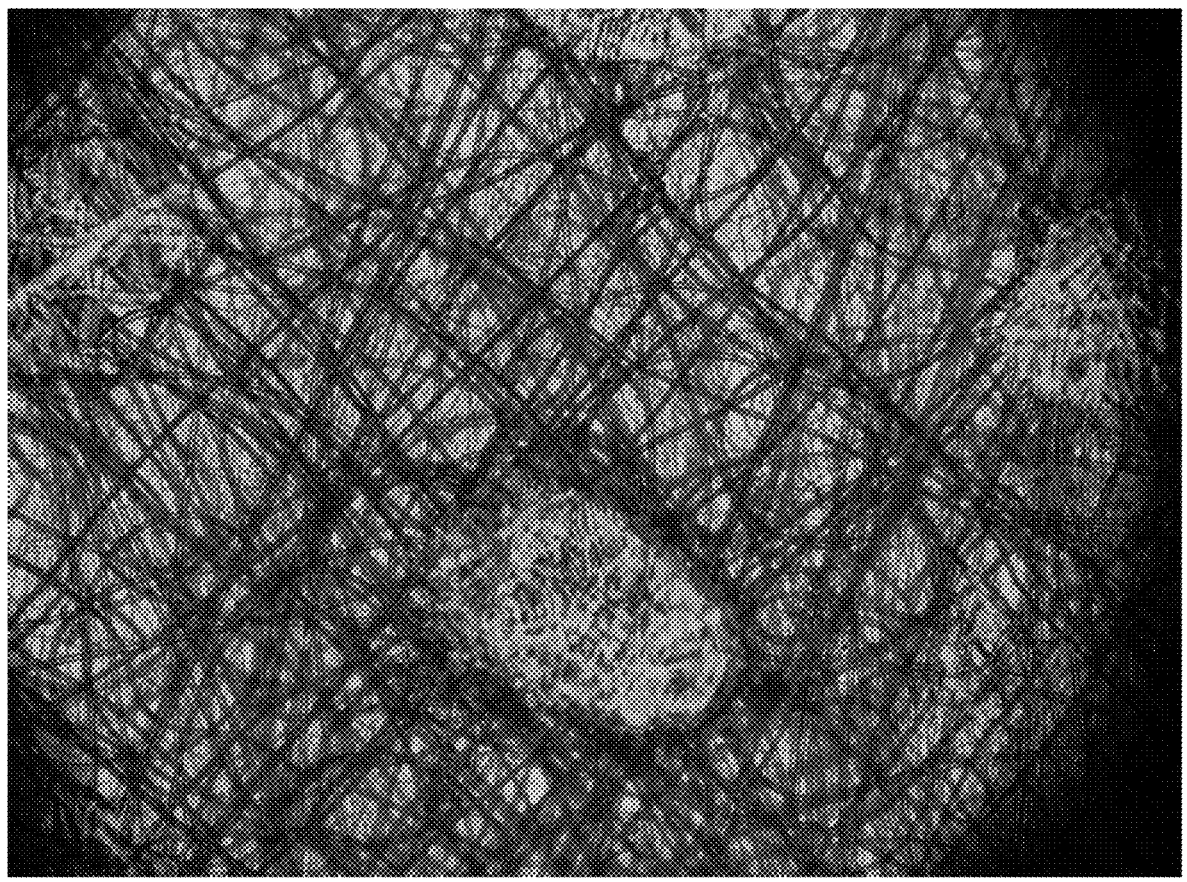
Figure 6:
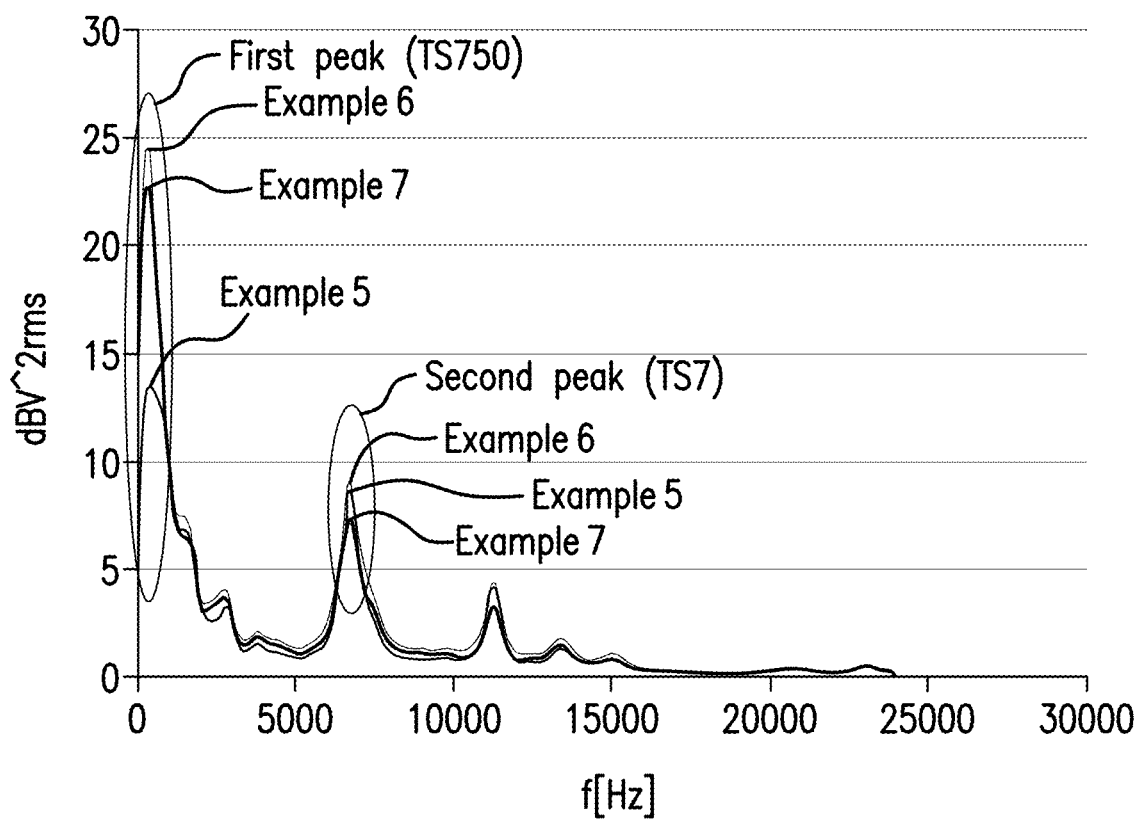

Further details and advantages of the present invention will be described with reference to the working examples and figures described in the following. The figures show:

FIG. 1: a schematic illustration of the structure of an SMS-type nonwoven laminate according to one embodiment of the present invention;

FIG. 2: a schematic illustration of an apparatus for producing such laminate;

FIG. 3: a schematic illustration of a section of a crimped multicomponent fiber as comprised in a high loft spunbond layer $S_H$ of such laminate;

FIG. 4: a micrograph of a high loft spunbond layer $S_H$ of such laminate;

FIG. 5: a micrograph of a standard loft spunbond layer $S_S$ of such laminate;

FIG. 6: TSA test results for the upper side of such laminate; and

Figure 7:
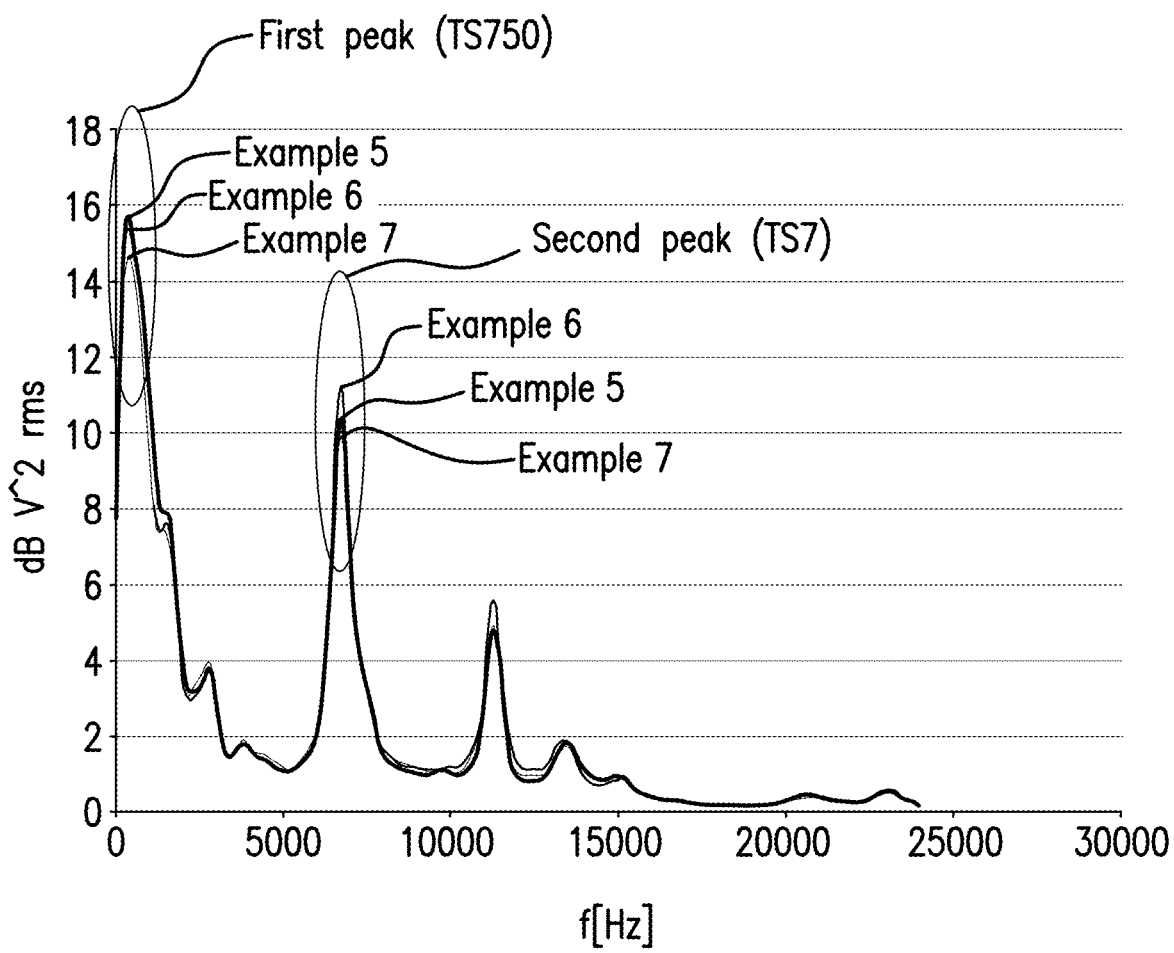

FIG. 7: TSA test results for the lower side of such laminate.

The values for molecular weight averages ($M_z$, $M_w$ and $M_n$), molecular weight distribution (MWD) and its broadness, described by polydispersity index, PDI=$M_w/M_n$ (wherein $M_n$ is the number average molecular weight and $M_w$ is the weight average molecular weight) as used herein are to be understood as having been determined by GPC (Gel Permeation Chromatography) according to ISO 16014-1:2003, ISO 16014-2:2003, ISO 16014-4:2003 and ASTM D 6474-12 using the following formulae:

$$M_n = \frac{\sum_{i=1}^{N} A_i}{\sum_{i=1}^{N} (A_i / M_i)} \quad (1)$$

$$M_w = \frac{\sum_{i=1}^{N} (A_i \times M_i)}{\sum_{i=1}^{N} A_i} \quad (2)$$

$$M_z = \frac{\sum_{i=1}^{N} (A_i \times M_i^2)}{\sum_{i=1}^{N} (A_i \times M_i)} \quad (3)$$

For a constant elution volume interval $\Delta V_i$, where $A_i$, and $M_i$ are the chromatographic peak slice area and polyolefin molecular weight (MW), respectively associated with the elution volume, $V_i$, where N is equal to the number of data points obtained from the chromatogram between the integration limits.

A high temperature GPC instrument, equipped with either infrared (IR) detector (IR4 or IR5 from PolymerChar (Valencia, Spain) or differential refractometer (RI) from Agilent Technologies, equipped with 3× Agilent-PLgel Olexis and 1× Agilent-PLgel Olexis Guard columns was used. As the solvent and mobile phase 1,2,4-trichlorobenzene (TCB) stabilized with 250 mg/L 2,6-Di tert butyl-4-methyl-phenol) was used. The chromatographic system was operated at 160° C. and at a constant flow rate of 1 mL/min. 200 µL of sample solution was injected per analysis. Data collection was performed using either Agilent Cirrus software version 3.3 or PolymerChar GPC-IR control software.

The column set was calibrated using universal calibration (according to ISO 16014-2:2003) with 19 narrow MWD polystyrene (PS) standards in the range of 0.5 kg/mol to 11 500 kg/mol. The PS standards were dissolved at room temperature over several hours. The conversion of the polystyrene peak molecular weight to polyolefin molecular weights is accomplished by using the Mark Houwink equation and the following Mark Houwink constants:

$K_{PS} = 19 \times 10^{-3}$ mL/g, $a_{PS} = 0.655$ $K_{PE} = 39 \times 10^{-3}$ mL/g, $a_{PE} = 0.725$ $K_{PP} = 19 \times 10^{-3}$ mL/g, $a_{PP} = 0.725$ A third order polynomial fit was used to fit the calibration data.

All samples were prepared in the concentration range of 0.5-1 mg/ml and dissolved at 160° C. for 2.5 hours.

The melt flow rates indicated in all examples correspond to those obtained according to ISO 1133-1 at 230° C. under 2160 g load.

EXAMPLES 1 TO 4

The following examples 1 to 4 demonstrate the surprising effect that when producing a spunbond nonwoven fabric the mixing of two polymers A and B in one polymer stream and maintaining polymer A in the other polymer stream of a side-by-side bicomponent fiber it is possible to create more crimp and thereby more bulk in the resulting web. The examples also demonstrate that this surprising effect is particularly emphasized when the melt flow rates of the two polymers A and B are different.

In each of these examples, a laminate comprising a standard loft spunbond layer and a high loft spunbond layer has been produced.

In examples 1 and 2, the standard loft spunbond bottom layer ($S_S$) first produced was formed entirely from a single PP Homopolymer with an MFR of 25, a PD of 4.68 and a quotient $M_z/M_w$ of 2.08 (Trade Name Moplen HP561R). In examples 3 and 4, the standard loft spunbond bottom layer ($S_S$) first produced was formed entirely from a single PP Homopolymer with an MFR of 35, a PD of 4.93 and a quotient $M_z/M_w$ of 2.07 (Trade Name Exxon 3155). In either case, 0.3 wt.-% of a colorant ($TiO_2$) was added as the only additive and the titer of the fibers was in the range of 1.6 to 1.8 denier.

In either of the examples 1 to 4, a high loft spunbond upper layer ($S_H$) formed entirely from circular side-by-side bicomponent fibers comprising 70 wt.-% of a first component and 30 wt.-% of a second component was laid onto the standard loft spunbond bottom layer ($S_S$) thus obtained. In either case, the first component comprised 69.7 wt.-% of polymer and 0.3 wt.-% of a colorant ($TiO_2$) as the only additive. In either case, the titer of the fibers was in the range of 1.6 to 1.8 denier.

In examples 1 and 2, the first component was formed entirely from the same polymer as used for the standard loft spunbond layer ($S_S$), the PP homopolymer having the trade name Moplen HP561R. Also in examples 3 and 4, the first component was formed entirely from the same polymer as used for the standard loft spunbond layer (Se), in this case the PP homopolymer having the trade name Exxon 3155.

In examples 1 and 3 (both comparative), the second component was formed from a single polymer, a PP homopolymer with an MFR of 25, a PD of 6.81 and a quotient $M_z/M_w$ of 2.91 (Trade Name Moplen HP552R).

In examples 2 (comparative) and 4 (inventive), the second component was formed from a 50/50 (by weight) blend of the same polymer as used for the first component (Moplen HP561R in example 2 and Exxon 3155 in example 4) and of the polymer Moplen HP552R. The melt flow rate of polymer Moplen HP561R is similar to the melt flow rate of polymer Moplen HP552R. The melt flow rate of polymer Exxon 3155 is 40% different the melt flow rate of polymer Moplen HP552R.

All four examples 1 to 4 were carried out under the same process conditions using the same machinery.

The physical properties of the webs obtained according to these examples are summarized in Table 1.

TABLE 1

| | | Example | |
|---|---|---|---|
| | | 1 (Comparative) | 2 (Comparative) |
| Lower spunbond layer ($S_S$) (monocomponent fiber) | 8.4 g/m² | 99.7 wt.-% HP561R<br>0.30 wt.-% $TiO_2$ | 99.7 wt.-% HP561R<br>0.30 wt.-% $TiO_2$ |
| Upper spunbond layer ($S_H$) (bicomponent fiber) | 8.4 g/m² | 69.7 wt.-% HP561R<br>0.30 wt.-% $TiO_2$<br>30 wt.-% HP552R | 69.7 wt.-% HP561R<br>0.30 wt.-% $TiO_2$<br>15 wt.-% HP552R<br>15 wt.-% HP561R |

TABLE 1-continued

| | | |
|---|---|---|
| Overall caliper [mm] | 0.23 | 0.28 |
| Overall density [g/cm³] | 0.073 | 0.060 |
| Upper layer density [g/cm³] | 0.056 | 0.042 |
| TSMD [N/50 mm] | 24.51 | 22.47 |
| TEMD [%] | 69.67 | 67.44 |
| TSCD [N/50 mm] | 14.16 | 12.02 |
| TECD [%] | 75.61 | 70.09 |

| | | Example | |
|---|---|---|---|
| | | 3 (Comparative) | 4 (Inventive) |
| Lower spunbond layer ($S_S$) (monocomponent fiber) | 8.4 g/m² | 99.7 wt.-% Exxon 3155<br>0.30 wt.-% TiO₂ | 99.7 wt.-% Exxon 3155<br>0.30 wt.-% TiO₂ |
| Upper spunbond layer ($S_H$) (bicomponent fiber) | 8.4 g/m² | 69.7 wt.-% Exxon 3155<br>0.30 wt.-% TiO₂<br>30 wt.-% HP552R | 69.7 wt.-% Exxon 3155<br>0.30 wt.-% TiO₂<br>15 wt.-% HP552R<br>15 wt.-% Exxon 3155 |
| Overall caliper [mm] | | 0.23 | 0.36 |
| Overall density [g/cm³] | | 0.072 | 0.046 |
| Upper layer density [g/cm³] | | 0.055 | 0.029 |
| TSMD [N/50 mm] | | 18.68 | 23.56 |
| TEMD [%] | | 56.93 | 67.58 |
| TSCD [N/50 mm] | | 10.57 | 12.54 |
| TECD [%] | | 65.95 | 74.95 |

TS means tensile strength. TE means tensile elongation. MD means machine direction. CD means cross machine direction.

Thickness of a material was measured according to WSP.120.6 (R4), Option A.

The overall density was calculated from the basis weight and caliper.

The upper layer density was calculated on the same basis, upon previously assuming that the lower layer comprises a caliper (thickness) at given basis weight according to standard spunbond materials (i.e., a thickness of approximately 0.08 mm) and subtracting this caliper from the value determined for the overall web.

Upon comparing the values for the upper layer density in the pairs of comparative and inventive examples 1/2 and 3/4, it becomes apparent that blending polymers according to the invention in the second component leads to an increase in loft. Surprisingly, this increase is particularly emphasized in the case of examples 3 and 4, where the components A and B have different melt flow rates.

With reference to examples 3 and 4, where the components A and B have different melt flow rates, it can further be observed that the tensile properties surprisingly improve in example 4 over example 3 irrespective of the higher loft.

EXAMPLES 5 TO 7

In all these examples SMMS nonwoven laminates are produced by identical spunmelt processes.

In either example, the first layer is a standard spunbond layer ($S_S$) comprising monocomponent fibers having a titer of 1.7 denier. The polymer used for these fibers is the polymer Exxon 3155 already described in connection with examples 1 to 4.

The two center layers M1 and M2 consist of meltblown fibers with a size of 3 to 5 μm. The polymer used is a PP homopolymer (HL508FB).

The top layers are formed by a high loft spunbond upper layer ($S_H$) which is formed entirely from circular side-by-side bicomponent fibers comprising 70 wt.-% of a first component and 30 wt.-% of a second component as described in table 2. The titer of the fibers was 1.7 denier.

Ercuamide is a slip-agent which has been added to both components in example 7.

In order to evaluate the composites materials barrier property the materials Hydrohead, Air Permeability and Pore size has been measured together with the materials basis weight and calliper.

As apparent from table 2, hydrohead air permeability and pore size has proven essentially unaffected for both inventive examples 6 and 7 as compared to the reference material of comparative example 5.

At the same time, however, the bulk/calliper has been increased by more than 100% for both inventive examples 6 and 7 as compared to the reference material of comparative example 5.

TABLE 2

| | | Example | |
|---|---|---|---|
| | | 5 (Comparative) | 6 (Inventive) |
| Lower spunbond layer ($S_S$) (monocomponent fiber) | 6.5 g/m² | 99.7 wt.-% Exxon 3155<br>0.30 wt.-% TiO₂ | 99.7 wt.-% Exxon 3155<br>0.30 wt.-% TiO₂ |
| First meltblown layer (M1) | 1 g/m² | 100 wt.-% HL508FB | 100 wt.-% HL508FB |
| Second meltblown layer (M2) | 1 g/m² | 100 wt.-% HL508FB | 100 wt.-% HL508FB |
| Upper spunbond layer ($S_H$) (bicomponent fiber) | 6.5 g/m² | 69.7 wt.-% Exxon 3155<br>0.30 wt.-% TiO₂<br>30 wt.-% Exxon 3155 | 69.7 wt.-% Exxon 3155<br>0.30 wt.-% TiO₂<br>15 wt.-% HP552R<br>15 wt.-% Exxon 3155 |

TABLE 2-continued

| | | |
|---|---|---|
| Overall caliper [mm] | 0.16 | 0.34 |
| Overall density [g/cm³] | 0.095 | 0.045 |
| Air permeability [l/m²/s] | 2018 | 1997 |
| Hydrohead [mm H₂O] | 171.0 | 161.4 |
| Pore size [%] | 98.8 | 98.3 |

| | | Example 7 (Inventive) |
|---|---|---|
| Lower spunbond layer ($S_S$) (monocomponent fiber) | 6.5 g/m² | 98.9 wt.-% Exxon 3155 |
| | | 0.30 wt.-% TiO₂ |
| | | 0.80 wt.-% Erucamide |
| First meltblown layer (M1) | 1 g/m² | 100 wt.-% HL508FB |
| Second meltblown layer (M2) | 1 g/m² | 100 wt.-% HL508FB |
| Upper spunbond layer ($S_H$) (bicomponent fiber) | 6.5 g/m² | 68.9 wt.-% Exxon 3155 |
| | | 0.30 wt.-% TiO₂ |
| | | 0.80 wt.-% Erucamide |
| | | 14.6 wt.-% HP552R |
| | | 14.6 wt.-% Exxon 3155 |
| | | 0.80 wt.-% Erucamide |
| Overall caliper [mm] | | 0.33 |
| Overall density [g/cm³] | | 0.046 |
| Air permeability [l/m²/s] | | 2034 |
| Hydrohead [mm H₂O] | | 164.2 |
| Pore size [%] | | 98.7 |

A schematic illustration of the nonwoven materials of examples 6 and 7 is given in FIG. 1. A schematic illustration of an apparatus which may be used to obtain such laminates is given in FIG. 2. The different layers are labelled $S_H$, $S_S$, M1 and M2 as above.

FIG. 3 is a schematic illustration of a section of a crimped endless fiber as present in the $S_H$ layer. FIG. 4 is a micrograph of the $S_H$ layer of example 7 where helically crimped sections of some fibers have been highlighted. As apparent, the crimped fiber sections form circles with an area of approximately 20.000 µm² to 50.000 µm² resulting in a crimp radius of between approximately 80 µm to 125 µm. Exemplary data actually measured are given in table 3 below:

TABLE 3

| Area [µm²] | Radius [µm] |
|---|---|
| 34.000 | 103 |
| 21.000 | 81 |
| 25.000 | 89 |
| 27.000 | 92 |
| 35.000 | 106 |
| 48.000 | 124 |
| 29.000 | 97 |
| 42.000 | 115 |

FIG. 5 is a micrograph of the $S_H$ layer as of example 5 to 7. It shows the traditional spunbond fibers. It is seen that these fiber have a straight character with no tendency to crimp. In the background, the 3 to 5 µm thin meltblown fibers from layers M1 and M2 can be seen.

For examples 5 to 7, the surface structure and softness was tested according to the measurement as described in the TSA Leaflet Collection No. 11 of 13 Nov. 2014 issued by emtec Electronic GmbH, Leipzig, DE. The results for the upper surface ($S_H$ in the inventive examples) of the laminate for each example are illustrated in FIG. 6. The results for the lower surface ($S_S$ in the inventive examples) of the laminate for each example are illustrated in FIG. 7.

As apparent from FIG. 6, the value of first peak for the reference material of example 5 is in the range of 13 dB and the values for inventive examples 6 and 7 are in the range of 22 to 24 dB and hence significantly higher. This shows that the surface of this side of the nonwovens with helically crimped/curled fibers has a more open surface topography with a bigger variance and more hills and valleys, indicative of the low density of this side of the material.

The value of the second peak is indicative of the softness of the individual fibers. Here it is seen that the individual fibers of the comparative example 5 and inventive example 6 are on same softness level, but the fibers of inventive example 7 containing Erucamide display a reduction in the peak value, which is an indication that the individual fibers are softer. The second peak value of examples 5 and 6 are approximately 8.3 dB and the value for example 7 containing Erucamide is approximately 7.0 db. Hence, upon addition of this agent, a reduction of almost 16% in individual fiber stiffness or an increase of almost 16% in individual fiber softness is observed.

As apparent from FIG. 7, the first peak values for all examples are within about 1 dB and in line with the first peak value of the upper side of reference example 5, meaning that in example 5 the two sides have an identical surface topography.

In the second peak value the values are within a narrow span, which indicates similar fiber softness. However, also in this graph it becomes apparent that example 7, where the lower $S_S$ layer contains Erucamide, displays the lowest value, which indicates that this option has the softest individual fiber.

The invention claimed is:

1. A fabric comprising at least one high loft spunbond nonwoven layer ($S_H$) having crimped multicomponent fibers, wherein
   a first component of the multicomponent fibers comprises a first polymer A and a second component of the multicomponent fibers comprises a blend of the first polymer A and a second polymer B, wherein the melt flow rate of polymer A is at least 25% higher than the melt flow rate of polymer B and wherein the second component comprises at least 20 wt.-% of polymer B and wherein both polymer A and polymer B are selected from the group consisting of polypropylene (PP) homopolymers, polyethylene (PE) homopolymers, polyethylene-polypropylene (PP-PE) copolymers consisting of ethylene and propylene units, and blends of polypropylene (PP) homopolymers and polyethylene (PE) homopolymers.

2. The fabric of claim 1, wherein the melt flow rate of polymer A is at least 35% higher than the melt flow rate of polymer B and/or wherein the melt flow rate of polymer B is smaller or equal 26 g/10 min and the melt flow rate of polymer A is 34 g/10 min or greater, the melt flow rate obtained according to ISO 1133-1 at 230° C. under 2160 g load.

3. The fabric of claim 1, wherein the fabric further comprises at least one meltblown layer (M) or at least one standard loft spunbond layer ($S_S$) or both, where these additional layers form a nonwoven laminate with the at least one high loft layer spunbond layer ($S_H$).

4. The fabric of claim 3, wherein the melt blown layer (M) or the standard loft spunbond layer ($S_S$) or both are made of a thermoplastic polymer.

5. A method of manufacturing an SMS-type nonwoven laminate according to claim 3, which comprises the steps of:
   (a) providing the at least one standard loft spunbond layer ($S_S$) or high loft spunbond layer ($S_H$);
   (b) forming the at least one meltblown layer (M) upon depositing meltblown fibers on the surface of the standard loft spunbond layer ($S_S$) or high loft spunbond layer ($S_H$) provided under (a); and
   (c) forming the at least one high loft spunbond layer ($S_H$) or standard loft spunbond layer ($S_S$) upon depositing spunbond fibers on the surface of the meltblown layer (M) formed under (b).

6. A method of manufacturing an $S_H S_S S_H$-type nonwoven laminate according to claim 3, which comprises the steps of:
   (a) providing the at least one high loft spunbond layer ($S_H$);
   (b) forming the at least one standard loft spunbond layer ($S_S$) upon depositing spunbond fibers on the surface of the high loft spunbond layer ($S_H$) provided under (a); and
   (c) forming the at least one high loft spunbond layer ($S_H$) upon depositing spunbond fibers on the surface of the standard loft spunbond layer ($S_S$) formed under (b).

7. A method of manufacturing an $S_H S_S$-type nonwoven laminate according to claim 3, which comprises the steps of:
   (a) providing the at least one standard loft spunbond layer ($S_S$);
   (b) forming the at least one high loft spunbond layer ($S_H$) upon depositing spunbond fibers on the surface of the standard loft spunbond layer ($S_S$) formed under (a).

8. The fabric of claim 1, wherein the second polymer B has a different molecular weight distribution than the first polymer A.

9. The fabric of claim 1, wherein the difference in polydispersity indices between the polymers A and B is greater than 0.5.

10. The fabric of claim 1, wherein the polydispersity index of polymer A is between 4.0 and 6.0.

11. The fabric of claim 1, wherein the weight ratio of the first to second component in the multicomponent fibers is 40/60 to 90/10.

12. The fabric of claim 1, wherein the polymer of the first component or the polymer blend of the second component or the polymer of the $S_S$ layer or the polymer of the M layer or any combination thereof comprises an additive which is capable of enhancing the softness of the fiber.

13. The fabric of claim 1, wherein the linear mass density of the crimped multicomponent fibers is 1.4 to 2.6 or wherein the average crimp diameter of the crimped multicomponent fibers is 50 to 500 μm or both.

14. The fabric of claim 1, wherein the density of the high loft spunbond layer ($S_H$) is 0.02 to 0.08 g/cm$^3$.

15. A hygiene product comprising the fabric of claim 1 and optionally further comprising granular absorbent material.

16. The fabric claim 1, wherein the fabric further comprises at least one meltblown layer (M) or at least one standard loft spunbond layer ($S_S$) or both, where these additional layers form an $S_H M S_S$-type nonwoven laminate.

17. The fabric claim 1, wherein the fabric further comprises at least one meltblown layer (M) or at least one standard loft spunbond layer ($S_S$) or both, where these additional layers form an $S_H S_S S_H$-type nonwoven laminate.

18. The fabric claim 1, wherein the fabric further comprises at least one meltblown layer (M) or at least one standard loft spunbond layer ($S_S$) or both, where these additional layers form an $S_H S_S$-type nonwoven laminate.

19. The fabric of claim 1, wherein the second component comprises at least 40 wt.-% of said polymer B.

* * * * *